Figure 1:
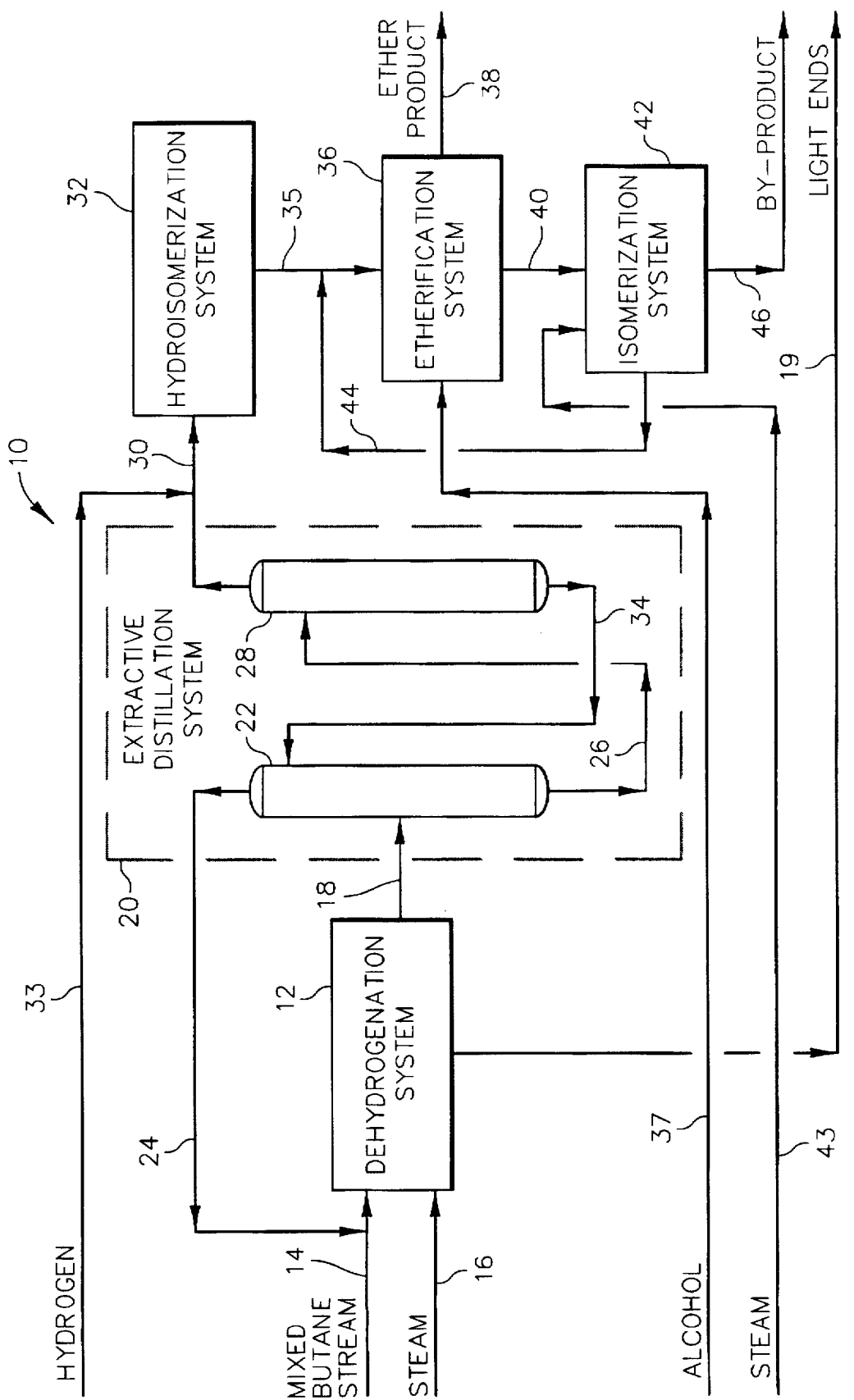

United States Patent [19]

Scharre et al.

[11] Patent Number: 5,750,798
[45] Date of Patent: May 12, 1998

[54] METHOD FOR MAKING ETHER FROM A PARAFFIN FEEDSTOCK

[75] Inventors: Mark D. Scharre; Warren M. Ewert; Harold R. Hunt, all of Bartlesville, Okla.

[73] Assignee: Phillips Petroleum Company, Bartlesville, Okla.

[21] Appl. No.: 573,219

[22] Filed: Dec. 13, 1995

[51] Int. Cl.$^6$ ............................................. C07C 41/06
[52] U.S. Cl. .................................... 568/697; 585/314
[58] Field of Search ........................... 568/697; 585/314

[56] References Cited

U.S. PATENT DOCUMENTS

| | | | |
|---|---|---|---|
| 4,513,153 | 4/1985 | Sandrin | 569/697 |
| 4,558,168 | 12/1985 | Gussow et al. | 585/324 |
| 5,237,115 | 8/1993 | Makovec et al. | 585/314 |
| 5,254,748 | 10/1993 | Hensley et al. | 568/697 |
| 5,382,707 | 1/1995 | Rubin et al. | 568/697 |
| 5,399,787 | 3/1995 | Ozmen et al. | 568/697 |

*Primary Examiner*—Paul J. Killos
*Assistant Examiner*—Sreeni Padmanabhan
*Attorney, Agent, or Firm*—Charles W. Stewart

[57] ABSTRACT

A process for the production of ethers from a paraffin feedstock. The process includes a novel arrangement of dehydrogenation, isomerization, hydroisomerization, separation and etherification to provide a novel method for the production of ethers from a paraffin feedstock.

10 Claims, 1 Drawing Sheet

1

METHOD FOR MAKING ETHER FROM A PARAFFIN FEEDSTOCK

The present invention relates to a method for manufacturing ether compounds from a paraffin feedstock.

Certain ether compounds are known to be desirable gasoline blending components. Among these ether compounds, alkyl tertiary alkyl ether is one of the most desirable for blending with gasoline. Such ether compounds can be prepared by reacting primary or secondary alcohols with olefin compounds having a double bond on a tertiary carbon atom in the presence of an acidic ionic exchange resin catalyst. The particularly more common etherification reactions are those that involve reacting methanol with either isobutylene or isoamylene to form respectively methyl tertiary butyl ether (MTBE) and methyl tertiary amyl ether (TAME). These tertiary alkyl ether compounds are particularly useful as octane improves for gasoline and, because of their low vapor pressure, they are particularly useful for reducing the vapor pressure of gasoline. It can be desirable to manufacture ether compounds from paraffin hydrocarbon, particularly, from butanes.

It is thus an object of this invention to provide a process for producing ether compounds from a paraffin feedstock.

According to the present invention, an ether product is produced by charging a mixed butane stream to a dehydrogenation system for dehydrogenating paraffin compounds to provide a dehydrogenate stream containing butene and diolefin. The dehydrogenate stream is passed to an extractive distillation system utilizing a suitable extraction solvent to separate paraffins and olefins and providing a first overhead stream containing at least one paraffin compound and a second overhead stream containing at least one olefin compound and at least one diolefin compound. The second overhead stream is passed to a hydroisomerization system whereby at least a portion of the diolefin concentration is hydrogenated to produce a hydroisomerate stream having a concentration of diolefin less than the concentration of diolefin in the second overhead stream. The hydroisomerate stream is passed to an etherification system whereby the isoolefin is reacted with a primary alcohol to produce an ether product, containing ether, and a raffinate stream, containing linear butenes. The raffinate stream is charged to an isomerization system to isomerize at least a portion of the linear butene contained in the raffinate stream to isobutene to produce an isomerate stream containing isobutene.

In the accompanying drawing:

FIG. 1 provides a schematic representation of one embodiment of the inventive process.

The inventive process utilizes a novel arrangement of subprocess systems and separation means to give an overall integrated process system that provides for the processing of paraffins, particularly butanes, so as to produce an ether end-product. In this process, a paraffin feed stream is first charged to a dehydrogenation system for dehydrogenating dehydrogenatable hydrocarbons to produce olefin compounds using a reactor zone containing therein a steam active dehydrogenation catalyst. The paraffin feed stream is contacted with the steam active dehydrogenation catalyst under process conditions suitable for promoting the dehydrogenation of the paraffin compounds to thereby produce olefin compounds.

Any suitable steam active dehydrogenation catalyst can be used, but the most particularly suitable steam active dehydrogenation catalyst comprises (1) a support selected from the group consisting of alumina, silica, magnesia, zirconia, alumina-silicates, Group II aluminate spinels and mixtures thereof and (2) a catalytic amount of at least one Group VIII metal. (Groups of metals as referred to herein are the groups of metals as classified in the Periodic Table of the Elements as set forth in Chemical Rubber Company's "Handbook of Chemistry and Physics", 45th Edition (1964), page B-2).

Any catalytically active amount of Group VIII metal can be employed in the steam active dehydrogenation catalysts. Generally the Group VIII metal is present in the catalyst in an amount in the range of from about 0.01 to about 10 weight percent of the weight of the support, more often about 0.1 to about 5 weight percent.

Other suitable copromoter metals can also be employed in the steam active dehydrogenation catalyst in conjunction with the Group VIII metal. A preferred type of such co-promoters are Group IVa metal can exist in the range of about 0.1–1 weight percent of said support and in one further embodiment, can exist in the range of about 0.1–0.5 weight percent of said support. Although any Group IVa metal, when in compound form, is fully within the scope of this invention, some convenient compounds are the halides, nitrates, oxalates, acetates, carbonates, propionates, tartrates, bromates, chlorates, oxides, hydroxides, and the like of tin, germanium and lead. Tin, itself, is the preferred Group IVa metal and impregnation of the support with tin compounds such as the stannous halides is particularly effective and convenient.

Generally speaking, the Group VIII and Group IVa compounds, which can be combined with the supports to form the catalysts used in the dehydrogenation process can be any compound in which all elements, other than those of Group VIII or Group IVa are volatilized during calcination. These compounds can be sequentially combined with the support, in any order, or for convenience, can be applied simultaneously in a single impregnation operation. After impregnation, the composite solids are dried and calcined.

The dehydrogenation is conducted under any suitable operating conditions. Generally, the dehydrogenation is carried out such that the temperature in the inlet portion of the catalyst beds is at a temperature in the range of about 900° F. to about 1200° F., preferably about 950° F. to about 1150° F. The dehydrogenation is also conducted at a pressure in the range of about 0 to about 200 psig, preferably about 0 to about 100 psig.; Generally, the molar ratio of steam to hydrocarbon is in the range of about 1/1 to about 25/1, preferably about 2/1 to 10/1. The use of an externally heated reactor, i.e., a reactor within a fired furnace, enables one to carry out the present invention with the lower levels of steam. The liquid hourly space velocity of hydrocarbon, i.e., volume of hydrocarbon per volume of catalyst per hour, is generally in the range of about 0.5 to about 10, preferably about 2.0 to about 6.

The paraffin feed stream can comprise any dehydrogenatable hydrocarbon. The process is particularly suitable for paraffin hydrocarbons having from 3 to 8 carbon atoms per molecule. Most preferably, the dehydrogenatable hydrocarbon is selected from the group consisting of normal butane and isobutane.

The dehydrogenate stream from the dehydrogenation system, containing olefins, particularly butylene, is passed as a feed to an extractive distillation system. The extractive distillation system is utilized to separate paraffins and olefins, particularly, butanes from butenes. Because the close boiling temperatures of butanes and butenes, extractive distillation is required to be used to perform the separation as opposed to other separation methods such as conventional fractional distillation.

Extractive distillation is a known separation method and is described in detail in literature such as *Perry's Chemical Engineers' Handbook*, Sixth Edition, published by McGraw-Hill Company 1984, page 13–53 through 13–57 and U.S. Pat. No. 3,687,202, both of which are incorporated herein by reference.

Any conventional extraction solvent can be utilized in the extractive distillation system which permits the separation of the paraffins and olefins of the mixture. Examples of suitable extraction solvents include acetonitrile, dimethylformamide, furfural, acetone, dimethylacetamide, n-methylpyrridone, dimethylsulfoxide, sulfolane, and n-formylmorpholine. These solvents can be used alone or with a cosolvent such as water. The preferred extraction solvents include acetonitrile, n-methylpyrridone and sulfolane.

The dehydrogenate stream, comprising alkanes, alkenes, and diolefins that are either produced as an undesirable by-product of the dehydrogenation reaction or were part of the paraffin feed stream charged to the dehydrogenation system, is fed to an extractive distillation tower where it is contacted with a solvent. The solvent alters the relative volatilities of the alkanes and alkenes thereby permitting the separation of such compounds into a first overhead stream comprising at least one paraffin compound and a bottoms stream. The bottoms stream from the extractive distillation tower is passed to a stripping tower which provides a second overhead stream comprising at least one olefin and, in most instances, at least one diolefin compound.

The second overhead stream from the extractive distillation system is charged or passed to a hydroisomerization system, whereby diolefins are selectively hydrogenated to form olefins and at least a portion of the butene-1 of the second overhead stream can be isomerized to butene-2 to produce a hydroisomerate stream having a concentration of diolefin less than the concentration of diolefin in the second overhead stream but which is less than about 200 parts per million weight (ppmw), preferably less than about 100 ppmw, and most preferably, less than 20 ppmw.

The first overhead stream can be recycled as a feed to the dehydrogenation system for further processing. By recycling the first overhead stream to the dehydrogenation system, the paraffins that are charged to and are passed through the dehydrogenation system without being dehydrogenated to olefins are eventually reacted to extinction thereby converting substantially all the paraffins of the paraffin feed stream to olefins and small quantities of other generally undesirable by-products. Thus, the second overhead stream from the extractive distillation system should contain only a small amount of paraffins with the amount of paraffin depending on the separation efficiency of the extractive distillation system. It is preferred to minimize the amount of paraffins which pass with the second overhead stream and maximize the recovery of the paraffin of the dehydrogenate stream with the first overhead stream.

The catalysts utilized in the hydroisomerization unit of this invention comprise the noble metals of Group VIII of the Periodic Table of Elements, as listed in the *Handbook of Chemistry and Physics*, published by the Chemical Rubber Company, in the 49th Edition (1969), page B-3. The catalysts intended to be included in the group of nobel metals of Group VIII specifically are ruthenium, rhodium, palladium, osmium, iridium, and platinum.

Any of the usual catalyst supports can be employed, such as alumina (preferred), silica alumina, glass beads, and carbon. Catalysts in the form of pellets, spheres, and extrudates are satisfactory.

A preferred hydroisomerization catalyst is palladium on a carrier, the carrier preferably being alumina. The catalyst should contain from about 0.005 to about 2.0 percent palladium on alumina, preferably about 0.1 to about 1.0 weight percent palladium on alumina. Most preferably, the catalyst should contain from about 0.3 to abut 0.5 weight percent palladium on alumina. A suitable catalyst weighs about 40 to about 60 pounds per cubic foot, has a surface area of about 30 to about 150 square meters per gram, a pore volume of about 0.35 to about 0.50 mL per gram, and a pore diameter of about 200 to about 500 Å.

As an example, a suitable commercial hydroisomerization catalyst satisfactory for use in this invention is manufactured by Mallinckrodt Specialty Chemicals Company, designated as Calsicat catalyst number E-144 SDU. The commercial catalyst contains about 0.55 weight percent palladium on alumina.

The hydroisomerization process is conducted at a reaction temperature of about 100° to about 300° F., preferably 130°–200° F.

The hydroisomerization process of this invention can be most effectively practiced at relatively low pressure conditions while maintaining the hydrocarbon most preferably in the liquid phase, although vapor phase operation can be used. Pressures employed for the liquid phase process are from about 100 to about 600 psig, preferably from about 150 to about 300 psig. Liquid hourly space velocities, LHSV, are maintained from about 2 to about 50, preferably from about 3 to about 10.

Hydrogen is utilized in the hydroisomerization process by preferably being mixed with the hydrocarbon feed stream prior to contacting the stream with the hydroisomerization catalyst. The hydrogen is necessary to effect double bond isomerization of the 1-olefin with the hydroisomerization catalysts and to provide for hydrogenation of diolefins to olefins. The hydrogen is added in amounts from 0.1 to 20.0 mole percent, preferably in amounts of about 1.0 to about 10.0 mole percent.

The hydroisomerate stream from the hydroisomerization unit, generally comprising isobutylene, butene-1, butene-2 and at least one paraffin compound, is charged or passed to an etherification system whereby the isoolefins present in the second overhead stream are converted to ethers by reaction with primary or secondary alcohols in the presence of an acid ion exchange resin catalyst. Generally, the isoolefins include those hydrocarbons having 4 to 16 carbon atoms per molecule. Examples of such isoolefins include isobutylene, isoamylene, isohexylene, isoheptylene, isooctylene, isononylene, isodecylene, isoundecylene, isododecylene, isotridecylene, isotetradecylene, isopentadecylene, and isohexadecylene, or mixtures of two or more thereof.

The alcohols which may be utilized in the etherification reaction include the primary and secondary aliphatic alcohols having from 1 to 12 carbon atoms, such as methanol, ethanol, propanol, isopropanol, the primary and secondary butanols, pentanols, hexanols, ethylene glycol, propylene glycol, butylene glycol, the polyglycols, and glycerol, etc., or mixtures of two or more thereof.

The presently preferred reactants of the etherification reaction are methanol and isobutylene and/or an amylene because they respectively yield methyl tertiary butyl ether (MTBE) and tertiary amyl methyl ether (TAME) which have utility as octane improvers for gasoline. Accordingly, it is currently preferred for the isoolefins to be predominately isobutylene and isoamylene compounds with the double bond on the tertiary carbon atom and the alcohol predominately methanol. Another embodiment of this invention includes the use of the reactants ethanol and isobutylene to yield ethyl tertiary butyl ether (ETBE).

It is generally preferred for the isoolefin and the alcohol to be passed through the etherification reaction zone in the presence of diluents which do not have an adverse effect upon the etherification reaction. Examples of suitable diluents include alkanes and straight chain olefins. The feed to the etherification reactor, excluding alcohol, is generally diluted so as to include about 2 to about 80 weight percent isoolefin, preferably about 10 to about 50 weight percent.

The acid ion-exchange catalysts useful in the etherification reaction zone of the etherification system are relatively high molecular weight carbonaceous material containing at least one $SO_3H$ functional group. These catalysts are exemplified by the sulfonated coals ("Zeo-Karb H", "Nalcite X" and "Nalcite AX") produced by the treatment of bituminous coals with sulfuric acid and commercially marketed as zeolitic water softeners or base exchangers. These materials are usually available in a neutralized form and in this case must be activated to the hydrogen form by treatment with a strong mineral acid such as hydrochloric acid and water washed to remove sodium and chloride ions prior to use. The sulfonated resin type catalyst are preferred for use in the present invention. The catalysts include the reaction products of phenolformaldehyde resins with sulfuric acid ("Amberlite IR-1", "Amberlite IR-100" and "Nalcite MX"). Also useful are the sulfonated resinous polymers of coumarone-indene with cyclopentadiene, sulfonated polymers of coumarone-indene with cyclopentadiene, and furfural and sulfonated polymers of cyclopentadiene and furfural. The most preferred cationic exchange resins are strongly acidic exchange resins consisting essentially of sulfonated polystyrene resin, for instance, divinylbenzene cross-linked polystyrene matrix having from 0.5 to 20 percent and preferably from 4 to 16 percent of copolymerized divinylbenzene therein to which are ionizable or functional nuclear sulfonic acid groups. These resins are manufactured and sold commercially under various trade names such as "Dowex 50", "Nalcite HCR" and "Amberlyst 15". As commercially obtained they have solvent contents of about 50 percent and can be used as is or the solvent can be removed first. The resin particle size is not particularly critical and therefore is chosen in accordance with the manipulative advantages associated with any particular size. Generally, mesh sizes of 10 to 50 U.S. Sieve Series are preferred.

The reaction may be carried out in either a stirred slurry reactor or in a fixed bed continuous flow reactor. The catalyst concentration in a stirred slurry reactor should be sufficient to provide the desired catalytic effect. Generally catalyst concentration should be 0.5 to 50 percent (dry basis) by weight of the reactor contents with from 1 to 25 percent being the preferred range.

Acid ion exchange resins, such as Rohm & Haas Amberlyst 15 and Dow Chemical Dowex M-31, are currently the most preferred catalysts for the etherification.

The temperature for the etherification reaction zones and the space velocity for the feed to the etherification reactor zone can be selected as desired depending upon the degree of conversion desired and the temperature at which oligomerization becomes a problem. Generally, the temperature of the reaction zone will be in the range of about 86° F. to about 248° F., preferably about 95° F. to about 176° F. Pressures are generally selected to ensure that the charges and the products remain in the liquid phase during the reaction. Typical pressures are in the range of about 30 to about 300 psig. Generally, the liquid hourly space velocity (LHSV) of feed in the reactors will be in the range of about 2 to about 50 $hr^{-1}$.

The molar ratio of alcohol to isoolefin in etherification system feed will generally be in the range of about 0.5/1 to about 4/1, preferably about 0.8/1 to 1.2/1, most preferably about 1/1.

The etherification reaction zone effluent is passed to a separation system within the etherification system for separating the etherification reaction zone effluent into an ether product stream, containing ether, and a raffinate stream, containing hydrocarbons that did not react within the etherification reaction zone and, preferably, linear butenes. Any suitable separation system known to those skilled in the art can be used to separate the etherification reaction zone effluent to provide the ether product stream and the raffinate stream. Generally, the etherification reaction zone effluent can pass to a conventional fractionator for separating ether from the remaining portion of the etherification reaction zone effluent to give an ether product stream. The remaining portion of the etherification reaction zone effluent is then passed to a solvent extraction system to separate alcohol and hydrocarbons. The alcohol can be recycled as a feed to the etherification reaction zone, and the separated unreacted hydrocarbons is passed from the etherification system as the raffinate stream.

The raffinate stream is passed to an olefin isomerization system for skeletally isomerizing the linear olefins to tertiary olefins, which can ultimately serve as a reactive feed in the etherification reactor zone, along with an added water and steam diluent, present in an amount of at least about 0.1 mole of water or steam per mole of olefin, to an isomerization reaction zone of the isomerization system containing an acidic alumina catalyst. The isomerization reaction is an equilibrium type reaction in which butene-2 is isomerized to isobutylene.

The acidic alumina catalysts utilized in the reaction zone of the isomerization system are those known in the art. Preferably, the alumina should have a surface area of at least 50 $m^2/g$. In the practice of the present invention, the alumina is used without the incorporation of substantial amounts of inert solids and does not contain substantial amounts of impurities. Good results are obtained with aluminas having a purity of at least about 99.50 weight percent. The alumina can be in any desired form suitable for contact with the olefin including, for example, granules, spheres, microspheres, pellets, tablets fluid powder, etc. Preferably alumina catalysts include catalytic beta-alumina and gamma-alumina. The isomerization catalyst can be employed in any manner conventional within the art, such as in a fixed bed, a fluidized bed and the like.

The isomerization reaction can be carried out either batch-wise or continuously, using a fixed catalyst bed, stirred batch reactor, a fluidized catalyst chamber, or other suitable contacting techniques. The isomerization process conditions should be suitable to carry out the conversion of the particular olefin involved. In general, the isomerization reaction can be carried out at a temperature from 600° F. to 1200° F., preferably from about 850° F. to about 1000° F. Any convenient pressure can be used, with the lowest practical pressure preferred in order to minimize side reactions such as polymerization. Pressures ranging from atmospheric to 200 psig are particularly suitable. The LHSV is generally in the range of about 0.1 to 30 volume liquid olefin/volume of catalyst/hr, preferably about 0.2–20.

The isomerization system serves to convert linear paraffins that are not reactive in the etherification system to tertiary olefin. The conversion of the linear paraffin to tertiary olefin allows for the recycling of the isomerate stream to the etherification system to be used as a reactive feedstock.

Now referring to FIG. 1, there is provided a schematic representation of process system 10 of this invention. A paraffin feedstream, preferably containing n-butane and isobutane, is charged to dehydrogenation system 12 by way of line 14. A steam diluent is charged to dehydrogenation system 12 by way of line 16. Passing from dehydrogenation system 12 by way of line 18 is a dehydrogenate stream, containing olefins, paraffins and diolefins. A light ends stream is removed from dehydrogenation system 12 through line 19.

The dehydrogenate stream passes to extractive distillation system 20 where it undergoes an extractive distillation utilizing a suitable extraction solvent to separate paraffins and olefins. Extractive distillation system 20 is a conventional extractive distillation system that utilizes a suitable extraction solvent to alter the relative volatilities of the alkanes and alkenes in the dehydrogenate stream in order to assist their separation. Thus, the dehydrogenate stream is charged to extractive distillation column 22 wherein it is contacted with an extraction solvent for removing butylenes. The butanes are passed as a first overhead stream by way of line 24 from extractive distillation column 22. The bottoms product from extractive distillation column 22 is passed by way of line 26 to stripper column 28. This bottoms stream contains butylenes removed from the dehydrogenate stream and solvent. Stripper column 28 serves to separate the extraction solvent from the butylenes. The separated butylenes pass as a second overhead stream by way of line 30 to hydroisomerization system 32. Hydrogen is mixed with the second overhead stream of line 30 by its addition through line 33. The bottoms product from stripper column 28 serves as the extraction solvent fed to extractive distillation column 22 by way of line 34.

The first overhead stream from extractive distillation system 20 can be recycled as a feed to dehydrogenation system 12. By charging the first overhead stream as a feed to dehydrogenation system 12, the paraffins of the paraffin feedstream that are not dehydrogenated to olefins by dehydrogenation system 12 are again passed to dehydrogenation system 12 ultimately resulting in the conversion of substantially all the paraffins charged with the paraffin feedstream to process system 10.

Hydroisomerization system 32 provides for the hydrogenation of the diolefins contained in the second overhead stream to olefins to provide a feedstock that can suitably be charged to etherification system 36. A hydroisomerate stream, which as a result of the hydroisomerization reaction contains a substantially reduced concentration of diolefin, is passed by way of line 35 to etherification system 36 wherein the isobutylene reacts with a primary alcohol, provided through line 37, to form ether. Etherification system 36 provides an ether product, containing ether, which passes downstream from etherification system 36 by way of line 38. A raffinate stream containing linear butenes passes from etherification system 36 by way of line 40 and is charged as a feed to isomerization system 42. Steam is also charged as a feed to isomerization system 42 by way of line 43. Within isomerization system 42, the linear butenes of the raffinate stream are isomerized to tertiary butene so as to provide a suitable feedstock for etherification system 36. An isomerate stream containing isobutene is recycled as a feed to etherification system 36 by way of line 44 and undesirable by-products pass from isomerization system 42 by way line 46.

Calculated Example

To illustrate the inventive process shown in FIG. 1, this calculated example is provided. The material balance of the calculated example is provided in Table 1. The stream numbers shown in Table 1 correspond to those represented in FIG. 1. As the material balance of Table 1 shows, a mixed butane stream of normal butane and isobutane is charged to the process system with it significantly being converted to an ether product.

TABLE 1

Calculated Material Balance

| | Stream | | | | | | | | | | | | | |
|---|---|---|---|---|---|---|---|---|---|---|---|---|---|---|
| | 14 | 16 | 18 | 19 | 24 | 30 | 33 | 35 | 37 | 38 | 40 | 43 | 44 | 46 |
| Mass Flow LB/HR | | | | | | | | | | | | | | |
| Lights | 0.00 | 7206.11 | 0.00 | 7634.27 | 0.00 | 0.00 | 2.02 | 0.19 | 0.00 | 0.00 | 0.19 | 108.09 | 0.00 | 183.59 |
| BD | 0.00 | 0.00 | 48.93 | 0.00 | 0.00 | 48.93 | 0.00 | 0.00 | 0.00 | 0.00 | 0.00 | 0.00 | 0.00 | 0.00 |
| BUTENE | 0.00 | 0.00 | 2136.93 | 0.00 | 213.69 | 1923.23 | 0.00 | 1973.99 | 0.00 | 0.00 | 4296.72 | 0.00 | 2322.73 | 829.96 |
| C4H10 | 2906.17 | 0.00 | 2676.74 | 0.00 | 1873.72 | 803.02 | 0.00 | 803.02 | 0.00 | 0.00 | 4187.96 | 0.00 | 3384.94 | 808.95 |
| IC4H10 | 2906.17 | 0.00 | 2906.17 | 0.00 | 2906.17 | 0.00 | 0.00 | 0.00 | 0.00 | 0.00 | 0.00 | 0.00 | 0.00 | 0.00 |
| C5+ | 0.00 | 0.00 | 0.00 | 0.00 | 0.00 | 0.00 | 0.00 | 0.00 | 0.00 | 0.00 | 0.00 | 0.00 | 0.00 | 62.92 |
| C16H12 | 0.00 | 0.00 | 0.00 | 0.00 | 0.00 | 0.00 | 0.00 | 0.00 | 0.00 | 0.00 | 0.00 | 0.00 | 0.00 | 0.00 |
| IC4H8 | 0.00 | 0.00 | 2898.89 | 0.00 | 289.89 | 2609.00 | 0.00 | 2609.00 | 0.00 | 0.00 | 0.00 | 0.00 | 999.89 | 0.00 |
| CH4O | 0.00 | 0.00 | 0.00 | 0.00 | 0.00 | 0.00 | 0.00 | 0.00 | 2061.02 | 0.04 | 0.00 | 0.00 | 0.00 | 0.00 |
| MTBE | 0.00 | 0.00 | 0.00 | 0.00 | 0.00 | 0.00 | 0.00 | 0.00 | 0.00 | 5669.86 | 0.00 | 0.00 | 0.00 | 0.00 |
| Total | 5812.34 | 7206.11 | 10667.65 | 7634.27 | 5283.47 | 5384.19 | 2.02 | 5386.20 | 2061.02 | 5669.90 | 8484.87 | 108.09 | 6707.56 | 1885.41 |

That which is claimed is:

1. A process comprising the steps of:
  charging a mixed butane stream to a dehydrogenation system for dehydrogenating paraffin compounds of said mixed butane stream to provide olefins, said dehydrogenation system producing a dehydrogenate stream containing butene and diolefin;
  passing said dehydrogenate stream to an extractive distillation system whereby said dehydrogenate stream undergoes an extractive distillation utilizing a suitable extraction solvent to separate paraffins and olefins by providing a first overhead stream containing at least one paraffin compound and a second overhead stream containing at least one olefin compound and at least one diolefin compound;

passing said second overhead stream to a hydroisomerization system whereby at least a portion of the diolefin concentration of said second overhead stream is hydrogenated to produce a hydroisomerate stream having a concentration of diolefin less than the concentration of diolefin in said second overhead stream;

passing said hydroisomerate stream to an etherification system for reacting isoolefin with a primary alcohol to form ether to thereby produce an ether product containing ether and a raffinate stream containing linear butenes; and charging said raffinate stream to an isomerization system to isomerize at least a portion of the linear butene of said raffinate stream to isobutene and to produce an isomerate stream containing isobutene.

2. A process as recited in claim 1 further comprising the step of:

charging at least a portion of said first overhead stream to said dehydrogenation system.

3. A process as recited in claim 2 wherein said mixed butane stream comprises normal butane and isobutane.

4. A process as recited in claim 3 wherein said primary alcohol is selected from the group consisting of methanol and ethanol.

5. A process as recited in claim 4 wherein said ether of said ether product is selected from the group consisting of methyl tertiary butyl ether and ethyl tertiary butyl ether.

6. A process as recited in claim 1 further comprising the step of:

charging at least a portion of said isomerate stream to said etherification system.

7. A process as recited in claim 6 further comprising the step of:

charging at least a portion of said first overhead stream to said dehydrogenation system.

8. A process as recited in claim 7 wherein said mixed butane stream comprises normal butane and isobutane.

9. A process as recited in claim 8 wherein said primary alcohol is selected from the group consisting of methanol and ethanol.

10. A process as recited in claim 9 wherein said ether of said ether product is selected from the group consisting of methyl tertiary butyl ether and ethyl tertiary butyl ether.

* * * * *